United States Patent
Squirrell et al.

(10) Patent No.: US 7,176,003 B2
(45) Date of Patent: Feb. 13, 2007

(54) METHOD FOR DETERMINING THE LENGTH OF A NUCLEIC ACID MOLECULE

(75) Inventors: David James Squirrell, Salisbury (GB); Martin Alan Lee, Salisbury (GB)

(73) Assignee: The Secretary of State for Defence, Salisbury (GB)

( * ) Notice: Subject to any disclaimer, the term of this patent is extended or adjusted under 35 U.S.C. 154(b) by 608 days.

(21) Appl. No.: 10/220,330

(22) PCT Filed: Mar. 6, 2001

(86) PCT No.: PCT/GB01/00933

§ 371 (c)(1),
(2), (4) Date: Nov. 22, 2002

(87) PCT Pub. No.: WO01/66795

PCT Pub. Date: Sep. 13, 2001

(65) Prior Publication Data

US 2003/0143574 A1    Jul. 31, 2003

(30) Foreign Application Priority Data

Mar. 7, 2000   (GB) ................... 0005281.1

(51) Int. Cl.
*C12P 19/34* (2006.01)
*C12Q 1/68* (2006.01)
*C07H 21/04* (2006.01)
*G01N 21/64* (2006.01)

(52) U.S. Cl. .............. 435/91.2; 435/6; 536/23.1; 422/82.08

(58) Field of Classification Search ............. 435/6, 435/91.2, 283.1
See application file for complete search history.

(56) References Cited

U.S. PATENT DOCUMENTS 5,106,538 A    4/1992   Barma et al.

(Continued)

FOREIGN PATENT DOCUMENTS

WO    WO 96/41016    12/1996

(Continued)

OTHER PUBLICATIONS

J. Powell (1998) Enhanced concatemer cloning—a modification to the SAGE (Serial Analysis of Gene Expression) technique. Nucleic Acids Research. vol. 26, pp. 3445-3446.*

Lee, S.H., et al. (1998) Preimplantation diagnosis of non-deletion Duchenne muscular dystrophy (DMD) by linkage polymerase chain reaction. Molecular Human Reproduction. vol. 4, pp. 345-349.*

(Continued)

*Primary Examiner*—Kenneth R. Horlick
*Assistant Examiner*—Angela Bertagna
(74) *Attorney, Agent, or Firm*—Kilpatrick Stockton LLP

(57) ABSTRACT

A method of determining the length of a particular region within a nucleic acid, the method comprising a) subjecting a sample of the nucleic acid to a plurality of amplification reactions in which the region is amplified, wherein the time of the extension phase in each of the reactions is varied; b) monitoring the progress of the amplification reactions; c) determining the minimum time during which extension phase of the amplification is completed within each reaction mixture and relating that to the length of the sequence undergoing extension. The method, combined with melting point analysis, will allow percentage GC content of a sequence to be determined. Length analysis of this type can be used in diagnosis or analysis as well as in recombinant DNA technology to check for the presence of concatamers, and in taxonomic classification or forensics. Apparatus for use in the method is also described and claimed.

19 Claims, 4 Drawing Sheets

U.S. PATENT DOCUMENTS

| | | | |
|---|---|---|---|
| 5,106,540 A | | 4/1992 | Barma et al. |
| 5,354,668 A | | 10/1994 | Auerbach |
| 5,538,848 A | | 7/1996 | Livak et al. |
| 5,601,141 A | | 2/1997 | Gordon et al. |
| 6,174,670 B1 * | | 1/2001 | Wittwer et al. ................ 435/6 |

FOREIGN PATENT DOCUMENTS

| | | |
|---|---|---|
| WO | WO 98/24548 | 7/1998 |
| WO | WO 99/28500 | 6/1999 |
| WO | WO 99/42611 | 8/1999 |

OTHER PUBLICATIONS

Kveiborg, M.K., et al. (1999) Telomere shortening during aging of human osteoblasts in vitro and leukocytes in vivo: lack of excessive telomere loss in osteoporotic patients. Mechanisms of Ageing and Development. vol. 106, pp. 261-271.*

"The LightCycler™ —the Smartest Innovation for More Efficient PCR"*Biochemica*, 2:4-7 (1998).

Higuchi, et al., "Kinetic PCR Analysis: Real-time Monitoring of DNA Amplification Reactions", *Bio/Technology* 11:1026-1030 (1993).

* cited by examiner

METHOD FOR DETERMINING THE LENGTH OF A NUCLEIC ACID MOLECULE

This application claims priority to Great Britain Application No. 0005281.1 filed on Mar. 7, 2000 and International Application No: PCT/GB01/00933 filed on Mar. 6, 2001 and published in English as International Publication Number WO 01/66795 A1 on Sept. 13, 2001, the entire contents of each of which are hereby incorporated by reference.

The present invention relates to a method for measuring the length and optionally also the melting point of a nucleic acid sequence, to the use of this in for example, the determination of percentage GC content of the sequence, as well as apparatus for use in the method. This method can be used in a variety of diagnostic, analytical or research situations.

The length of DNA sequences can be of interest for various reasons. In genetic diagnosis or analysis for example, genetic defects caused by insertions, deletions, truncations or duplications will affect the overall length of a particular gene within the genome of a particular organism.

In research applications, genetic linkage analysis is frequently effected in order to determine the relationship of particular genes within a genome. In such instances, the distance between particular genes may be useful in establishing the function and nature of particular genes.

Much research has been done with reference to telomeres, DNA found at the end of the genome which appears to get shorter each time the cell duplicates and is therefore implicated in the ageing process. The length of telomeric DNA in a particular sample may therefore provide an indication as to the age of the host from which the sample was derived.

Other factors which may change the overall length of a particular region of DNA within a genome includes infection with a virus which incorporates itself into the host genome, as well as the presence of transposons. Detection of the presence of these entities may therefore be of use in diagnosis or in genetic analysis. The length of microsatellite regions forms the basis of DNA fingerprinting techniques presently applied in forensics. In recombinant DNA technology, cloning experiments usually require that nucleic acid sequences are incorporated into other sequences such as vectors or plasmids prior to expression in recombinant hosts organisms such as bacteria, or cells. Successful clones are usually judged by including selection markers such as antibiotic resistance in the constructs which provides a means of identifying those hosts which have been successfully transformed.

Occasionally, there are errors in the cloning process and concatenation occurs, where a sequence is included in more than one copy (a particular problem when the clones are formed using restriction enzymes which yield blunt ended constructs). Alternatively, homologous recombination may occur resulting in the deletion of some or all of the target sequence.

In addition, when using RT-PCR, alternative splicing variants of mRNA occur which alter the length of the overall amplified sequence.

At present, nucleic acid length analysis is generally carried out using gel electrophoresis in which DNA fragments are taken from the sample, optionally following amplification, and run on a gel. This process takes some considerable time and samples must be removed from the reaction vessel, giving rise to the risk of contamination or cross-contamination where more than one sample is tested at the same time.

Nucleic acid amplification reactions such as the Polymerase Chain Reaction (PCR) are very well known. PCR is a procedure for generating large quantities of a particular DNA sequence and is based upon DNA's characteristics of base pairing and precise copying of complementary DNA strands. Typical PCR involves a cycling process of three basic steps.

Denaturation: A mixture containing the PCR reagents (including the DNA to be copied, the individual nucleotide bases (A,T,G,C), suitable primers and polymerase enzyme) are heated to a predetermined temperature to separate the two strands of the target DNA.

Annealing: The mixture is then cooled to another predetermined temperature and the primers locate their complementary sequences on the DNA strands and bind to them.

Extension: The mixture is heated again to a further predetermined temperature. The polymerase enzyme (acting as a catalyst) joins the individual nucleotide bases to the end of the primer to form a new strand of DNA which is complementary to the sequence of the target DNA, the two strands being bound together.

Such processes are in widespread use in research as well as in diagnostics and forensics.

The applicants have now found a way of using methods such as these to rapidly determine or check the length of a region of a nucleic acid sequence, and if required also to determine the % GC content of the sequence According to the present invention, there is provided a method for analysing the length of a particular region within a nucleic acid, said method comprising
a) subjecting a sample of said nucleic acid to a plurality of amplification reactions in which said region is amplified, wherein the time of the extension phase in each of said reactions is varied;
b) monitoring the progress of said amplification reactions;
c) determining the minimum time required for the extension phase of the amplification to completely take place within the reaction mixture and relating that to the length of the sequence undergoing extension.

The expression "completely take place" as used herein, means that the amplification reaction is carried out such that amplicon corresponding to all of said region is produced during each cycle. In general, the region will be defined by and including forward and reverse primers used in the amplification reaction, and full-length product is obtained during a "complete" amplification reaction.

In the method of the invention, any method may be used to monitor the progress of the application.

Techniques or assays for monitoring the progress of amplification reactions are known in the art. Many of these assays use fluorescence monitoring techniques for example of the polymerase chain reaction (PCR). These techniques include both probe strand specific and generic DNA intercalator techniques that can be used on a few second-generation PCR thermal cycling devices.

Generic fluorescence PCR methods utilise DNA intercalating dyes that exhibit increased fluorescence when bound to double stranded DNA species. Fluorescence increase due to a rise in the bulk concentration of DNA during amplifications can be used to monitor reaction progress and to determine the initial target molecule copy number.

These generic fluorescence PCR methods monitor the rise in bulk concentration of nucleic acids without any time penalty. A single fluorescent reading can be taken at the same point in every reaction. End point melting curve analysis can be used to discriminate artefacts from amplicon, and to discriminate amplicons. Peaks of products can be seen at concentrations that cannot be visualised by agarose gel electrophoresis.

Fluorescence PCR strand specific methods utilise additional nucleic acid reaction components to monitor the progress of amplification reactions. These methods may use fluorescence energy transfer (FET) as the basis of detection. One or more nucleic acid probes are labelled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is excited at this emission wavelength such that it can accept the emission energy of the donor molecule by a variety of distance-dependent energy transfer mechanisms. A specific example of fluorescence energy transfer which can occur is Fluorescence Resonance Energy Transfer or "FRET". Generally the acceptor molecule accepts the emission energy of the donor molecule when they are in close proximity (e.g. on the same, or a neighbouring molecule). The basis of FET or FRET detection is to monitor the changes at donor emission wavelength. Where the acceptor is also a fluorescent molecule, the acceptor emission wavelengths may also be monitored.

There are two commonly used types of FET or FRET probes, those using hydrolysis of nucleic acid probes to separate donor from acceptor, and those using hybridisation to alter the spatial relationship of donor and acceptor molecules.

One particular assay for monitoring the progress of an amplification reaction is the Taqman™ assay as described in U.S. Pat. No. 5,538,848.

Hydrolysis probes are commercially available as TaqMan™ probes. These consist of DNA oligonucleotides which are labelled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibites 5' to 3' exonuclease activity. TaqMan™ probes are protected at the 3' end by phosphorylation to prevent them from priming Taq extension. If the TaqMan™ probe is hybridised to the product strand than an extending Taq molecule may also hydrolyse the probe, liberating the donor from acceptor as the basis of detection. The signal in this instance is cumulative, the concentration of free donor and acceptor molecules increasing with each cycle of the amplification reaction. In general however, detection methods that rely on hydrolysis such as the TAQMAN™ assay are less preferred in the context of this invention than those which utilise hybridisation phenomena. This is because hydrolysis processes are relatively slow. Therefore, it is necessary to ensure that delays occasioned as a result of the hydrolysis of the probe are taken into account when determining whether the extension phase has proceeded to completion or not.

Hybridisation probes are available in a number of guises. Molecular beacons are oligonucleotides that have complementary 5' and 3' sequences such that they form hairpin loops. Terminal fluorescent labels are in close proximity for FRET to occur when the hairpin structure is formed. Following hybridisation of molecular beacon to a complementary sequence the fluorescent labels are separated, so FRET does not occur, and this forms the basis of detection.

Pairs of labelled oligonucleotides may also be used. These hybridise in close proximity on a PCR product strand bringing donor and acceptor molecules together so that FRET can occur. Enhanced FRET is the basis of detection. Variants of this type include using a labelled amplification primer with a single adjacent probe.

An assay which utilises a combination of a single labelled probe and an intercalating dye is described in International Patent Application No. PCT/GB98/03560.

International Patent application No. PCT/GB99/00504 describes assay for detecting the presence of particular nucleic acid sequences which may be adapted to quantify the amount of the target sequence in the sample. In this assay, an amplification reaction is effected using a set of nucleotides, at least one of which is fluorescently labelled. Thus the amplification product has fluorescent label incorporated in it. The reaction is effected in the presence of a probe which can hybridise to the amplification product and which includes a reactive molecule which is able to absorb fluorescence from or donate fluorescent energy to said fluorescent labelled nucleotide. The reaction can then be monitored by measuring the fluorescence of said sample as this will alter during the course of the reaction as more product is formed which hybridises to the probe and gives rise to a FET or FRET interaction between them.

Using these techniques, it is possible to directly detect not only whether a particular target sequence is present within a sample (because amplification is taking place), but by appropriate manipulation of the data, to quantify the amount or determine when an amplification reaches completion. In particular, graphs plotting fluorescence against time or cycle number generally produces a sigmoidal plot peak which rises steeply as amplification progresses and the amount of DNA in the sample increases, but which then reaches a plateau as amplification becomes saturated.

Polymerase activity during the extension phase of an amplification reaction is characterised as "processivity". This relates to the number of bases per second which are incorporated into the product. Generally the amplification reaction mixture is held at the extension temperature in excess of the minimum time needed to allow the complete target sequence to be synthesised i.e. the entire region defined by the primers.

By carrying out multiple reactions in accordance with the invention, the time at which the extension phase is allowed to proceed is eventually reduced until it is too short to allow entire sequence to be produced.

This will inhibit the amplification reaction considerably. One strand of the incomplete amplicon product will no longer bind one of the amplification primers and therefore, will not undergo extension during subsequent cycles. In addition, the length of the amplicon product produced in this way will be shorter and therefore, it will not incorporate so much label material such as intercalating dye, used to monitor the process. Where probes are employed in the monitoring process, they may not bind to the short amplicons and thus affect the signal generated.

If each reaction is monitored, it will soon become clear at which time the extension phase of the process is insufficiently long. In particular, the amplification will not proceed at an appropriate rate. This can be determined absolutely if the initial concentration or copy number of the target is known, but using the method of the invention, it may more simply be determined by comparing the amplifications with those where the extension phase time is long enough to allow for full length product to be produced.

In addition, the short product produced as a result of incomplete extension steps may itself act as a primer in subsequent reactions. The efficiency of this reaction is lower than a reaction in which the amplification is proceeding using a short primer. The PCR copy number detection generally follows the equation:

$$Nc=N(1+E)^c$$

where N=initial copy number/concentration
C=cycle number
E=reaction efficiency
and E=100%=$(e^{0.6931})$ Consequently, an amplification reaction in which short products are acting as secondary primers will demonstrate complex biphasic kinetics. By continuously monitoring the fluorescence of the extension phase, this will become immediately apparent as the normally regular increase in signal which appears during the extension phase of the reaction as the reaction proceeds (See FIG. 5 hereinafter) will be distorted as the reaction proceeds, and as more short product able to prime subsequent reactions is produced.

This can then be related to the length of the sequence being investigated by correlating this with the activity of the particular polymerase being employed at the temperature of the reaction. Typical polymerases incorporate approximately 500 base pairs in less than 10 seconds at conventional temperatures found in amplification reactions such as the PCR.

Suitable amplification reactions comprise polymerase chain reactions (PCR) or ligase chain reactions (LCR), but in particular will comprise a PCR reaction.

Suitably, in the method of the invention, the plurality of amplification reactions are effected simultaneously.

Up to now, carrying out multiple different amplification reactions simultaneously was not possible if different timing were required in each vessel. This is because conventional block heaters used to effect thermal cycling could only heat all the multiple reaction wells at the same time using the same time profiles. Block heaters generally require that all wells were heated to similar temperatures.

However, in a particularly preferred embodiment of the present invention, the plurality of amplification reactions are effected in apparatus such as that described and claimed in WO 98/24548.

Apparatus of this type uses electrically conducting polymer to provide means of heating a reaction vessel. Electrically conducting polymers are known in the art and may be obtained from Caliente Systems Inc. of Newark, U.S.A. Other examples of such polymers are disclosed for instance in U.S. Pat. No. 5,106,540 and U.S. Pat. No. 5,106,538. Suitable conducting polymers can provide temperatures up to 300° C. and so are well able to be used in PCR processes where the typical range of temperatures is between 30° and 100° C.

By passing an electric current through these polymers, they are able to heat rapidly. The heating rate depends upon the precise nature of the polymer, the dimensions of polymer used and the amount of current applied. Preferably the polymer has a high resistivity for example in excess of 1000Ohm.cm$^{-1}$. The temperature of the polymer can be readily controlled by controlling the amount of electric current passing through the polymer, allowing it to be held at a desired temperature for the desired amount of time. Furthermore, the rate of transition between temperatures can be readily controlled after calibration, by delivering an appropriate electrical current, for example under the control of an electronic controller.

Furthermore, rapid cooling can also be assured because of the low thermal mass of the polymer.

In addition, the use of polymer as the heating element in a reaction vessel will generally allow the apparatus to take a more compact form than existing block heaters, which is useful when carrying out chemical reactions in field conditions such as in the open air, on a river, on a factory floor or even in a small shop.

The reaction vessels may take the form of a reagent container such as a glass, plastics or silicon container, with electrically conducting polymer arranged in close proximity to the container. In one embodiment of the vessel, the polymer is provided as a sheath which fits around the reaction vessel, in thermal contact with the vessel. The sheath can either be provided as a shaped cover which is designed to fit snugly around a reaction vessel or it can be provided as a strip of film which can be wrapped around the reaction vessel and secured.

The polymer sheath arrangement means that close thermal contact is achievable between the sheath and the reaction vessel. This ensures that the vessel quickly reaches the desired temperature without the usual lag time arising from the insulating effect of the air layer between the reaction vessel and the heater. Furthermore, a polymer sheath can be used to adapt apparatus using pre-existing reaction vessels. In particular, a strip of flexible polymer film can be wrapped around a reaction vessel of various different sizes and shapes.

Where a sheath is employed it may be advantageous for it to be perforated or in some way reticulated. This may increase the flexibility of the polymer and can permit even readier access by a cooling medium if the polymer is not itself used to effect the cooling.

In another embodiment, the polymer is provided as an integral part of the reaction vessel. The reaction vessel may be made from the polymer by extrusion, injection moulding or similar techniques. Alternatively, the reaction vessel may be manufactured using a composite construction in which a layer of the conducting polymer is interposed between layers of the material from which the vessel is made or in which the internal or external surfaces of the reaction vessel is coated with the polymer, or again in which the vessel is basically made of the polymer coated with a thin laminate of a PCR compatible material. Such vessels may be produced using lamination and/or deposition such as chemical or electrochemical deposition techniques as is conventional in the art.

Vessels which comprise the polymer as an integral part may provide particularly compact structures.

Where, as in the present invention, several reaction vessels are required for a particular series of reactions, the reaction vessels may be provided in an array.

Each of or each group of reaction vessels may have its own heating/cooling/time profile set by adjusting the applied current to that vessel or group of vessels. This provides a further and particularly important advantage of reaction vessels with polymer over solid block heaters or turbulent air heaters, in that individual vessels can be controlled independently of one another with their own thermal profile. It means that a relatively small apparatus can be employed to carry out a plurality of PCR assays at the same time notwithstanding that each assay requires a different operating condition.

Such an arrangement is particularly preferred for use in the method of the present invention, since the plurality of amplification reactions can be carried out simultaneously, notwithstanding that the time at which each vessel is held at the extension temperature will be different in each case.

In a particularly suitable apparatus for use in the present invention, the polymer itself is formed, for example, by injection molding, into wells which are integrated into a plate. An electrode is attached to each well, preferably arranged such that even heating of the well can be effected. In particular, the electrodes may be connected at in the region of the base of each well. The thickness of the polymer is suitably as low as possible consistent with structural rigidity and integrity. This reduces the time taken for the polymer to heat.

The electrodes associated with each well may be connected to an individual supply, or several electrodes associated with groups of wells may be connected to different, independently controlled electrical supplies. With this arrangement, the different reactions requiring differently timed temperature stages can be carried out at the same time as each well or group of wells has its own heating element. Furthermore, the cycling reactions can be effected rapidly.

Plates may contain any number of wells, but in order to comply with conventional practice, 96 or 384 wells may be present in the same plate.

When using apparatus of this type in accordance with the invention, each amplification reaction is effected in a well of a multi-well vessel, and each well is heated by supplying current to an electrically conducting polymer which comprises or is arranged to heat said well.

Suitable control means will be electronic instrumentation so that the various reactions may be carried out automatically.

The method of the invention can be carried out in conjunction with other assay methodologies in which multiple amplification reactions are used.

For example, the temperature at which various duplexes form or destabilise within a reaction is highly dependent upon the relative guanidine (G) and cytosine (C) content of the sequence. The bond which forms between these bases is relatively stronger than that formed between adenine (A) and tyrosine (T) bases. Consequently, the temperature at which a particular duplex will destabilise or "melt" is highly dependent upon the GC content of the sequence. Furthermore, the percentage GC content of an organism's genome is a recognised taxonomic signature for determining the affiliations of the organism, such as bacterium, especially at the genus level.

By determining both the length and the melting point of any particular duplex nucleic acid, it is possible to calculate the percentage GC content thereof. Melting point determinations can be carried out simultaneously with the length determinations as described above.

In order to achieve this, it is necessary to use an appropriate labelling system, which will allow detection of the point at which duplexes form or destabilise within the reaction mixtures, label means are suitably provided in the reaction mixture. The label is preferably a visible label such as a fluorescent label as described above which is able to signal the formation or destabilisation of said duplexes. Thus, the assay can be carried out at the same time as that of the present invention provided appropriate labels can be used. All that needs to be done in order to gather both sets of data simultaneously is to monitor the signals from the labels throughout the amplification reaction as well as the reaction temperature, and process the data in order to provide all the desired information.

For combined assays, of this type, labels which used either intercalating dyes or hybridisation probes are preferred over hydrolysis probes as these provide the option of visualising the point at which a duplex destabilises.

A particularly preferred label means is an intercalating dye such as SYBRGold™ or SYBRGreen™ or ethidium bromide. When duplexes form during the amplification reaction, dye becomes bound between strands, giving off a heightened signals as a result. Thus the signal increases when duplexes are formed in the reaction mixture and decrease when they then destabilise. By monitoring both the temperature in the reaction vessel and the signal from the dye, the temperature at which duplexes form or destabilise can be ascertained. This will be related to the GC content of the particular sequence amplified in the reaction.

Alternatively, where at least some of the sequence is known, the label means may utilise fluorescence energy transfer (FET) as the basis of detection as described above. In particular in this instance however, the label suitably comprises one in which one of the donor or acceptor molecule is provided on a labelled hybridisation probe which binds to the target sequence at a particular temperature. The other may comprise an intercalating dye as described above. When the probe binds the target strand, intercalating dye is brought into close proximity to the probe and FET takes place. As a result, a change in the fluoresence from the donor and/or acceptor molecule is noted, which is reversed when the probe "melts" from the target sequence. Systems which utilise single labelled probes and intercalating dyes are described and claimed in International Patent Application No. PCT/GB 98/03560.

Alternatively, one of the donor or acceptor components of the label means may be included in a nucleotide utilised in the amplification reaction, as described in International Patent Application No. PCT/GB99/00504.

Hybridisation probes such as dual labelled probes or "Scorpions" or some molecular beacons may also be suitable for a combined length/melt point analysis assay.

Particular probes will bind particular target sequences at characteristic temperatures. Thus by conducting a series of amplification reactions in the presence of different probes and measuring the temperature at which these probes bind or melt from the target sequence, will provide information as to whether or not the target sequence is present in the sample of the target sequence.

The particular type of labelling system which may be employed in any particular set of amplification reactions will depend upon the nature of the sample, the length of any conserved or target sequences etc. For most applications however, an intercalating dye label will be preferred as this provides a simple and cost effective method for determining hybridisation and melt analysis of an amplicon.

In particular, the signal generated when amplification product destabilises will be a preferred measurement, as this provides a clearer signal.

If desired, a sample of nucleic acid may be subjected to a plurality of different amplification reactions.

As used herein, the expression "different amplification reactions" means that different sequences or parts of sequences within a particular sample are amplified. Generally speaking, this will mean that different amplification primers are used in each reaction. The amplification primers are suitably designed such that they amplify sequences which are known to be conserved amongst known species from which the samples are taken, for a number of species such as bacteria, fungi or plants, where taxonomic analysis is being carried out.

As a result, the presence, length and % GC content of various nucleic acid regions within one sample may be determined simultaneously.

This facility might be particularly useful in the fields of DNA profiling and in taxonomic classification.

The apparatus described above provides an ideal vehicle for effecting any such combined assay, as not only may the extension time be controllable, but also the overall temperature profile may be adjusted to ensure that different amplifications within each well or group of wells will take place. The control means is suitably an automatic control means such as electronic instrumentation. By using a programmable controller for the electrical circuit connected to the polymer, a defined heating regime, for example a defined number of cycles of predetermined temperature stages to be established over predetermined time intervals and dwells can be pre-programmed using the apparatus, including employing different temperature and time profiles with different wells in the same apparatus at the same time.

The control means may include a temperature monitoring device such as a thermocouple, which monitors the temperature of the reaction vessel and feeds this information into the control system so that the desired regime of heating and/or cooling is adhered to and verified.

Alternatively, the temperature of the polymer may be monitored directly by measuring its resistivity, for example by arranging the polymer heating element as a resistor in a wheatstone bridge circuit arrangement. This avoids the use of other temperature measurement devices such as thermocouples.

Optionally, the apparatus further comprises artificial cooling means such as one or more fans. In addition, fluorescence detection devices such as luminometers may be provided in order to detect duplex formation or destabilisation. These are suitably arranged in close proximity to the wells so that signals from reagents therein are detected.

In use, wells containing samples under test are suitably conducted in one area of the reaction vessel or plate, and those containing the known samples for comparison are located in a different area of the vessel. In this way, the comparisons may be made directly and quickly.

Other components of the reaction wells will comprise reagents required for the amplification reaction to take place. These are well known in the art, and may include amplification primers, nucleotides, buffers, as well as label means as discussed above.

The method described above is particularly useful in taxonomic classification and identification of organisms. Nucleic acids and, in particular, DNA from the organism is extracted and placed into a series of test wells. The amplification reaction conditions and the primers used are set such tat in each well, a sequence that is known to be characteristic of a particular organism, or conserved amongst several organisms, would be amplified if present. By obtaining information regarding the length and the %GC content of this sequence as described above, rapid taxonomic classification may be obtained.

Similarly in forensic or genetic analysis, a nucleic acid sample from a crime scene or a subject, may be compared with that of a suspect or of a perceived relative of the subject. By determining the lengths and/or % GC content of sufficient different nucleic acid sequences, it would be possible to determine whether the sample nucleic acid is from the same source or related to that of the comparative nucleic acid.

BRIEF DESCRIPTION OF THE DRAWINGS

The invention will now be particularly described by way of example with reference to the accompanying diagrammatic drawings in which.

Figure 1:
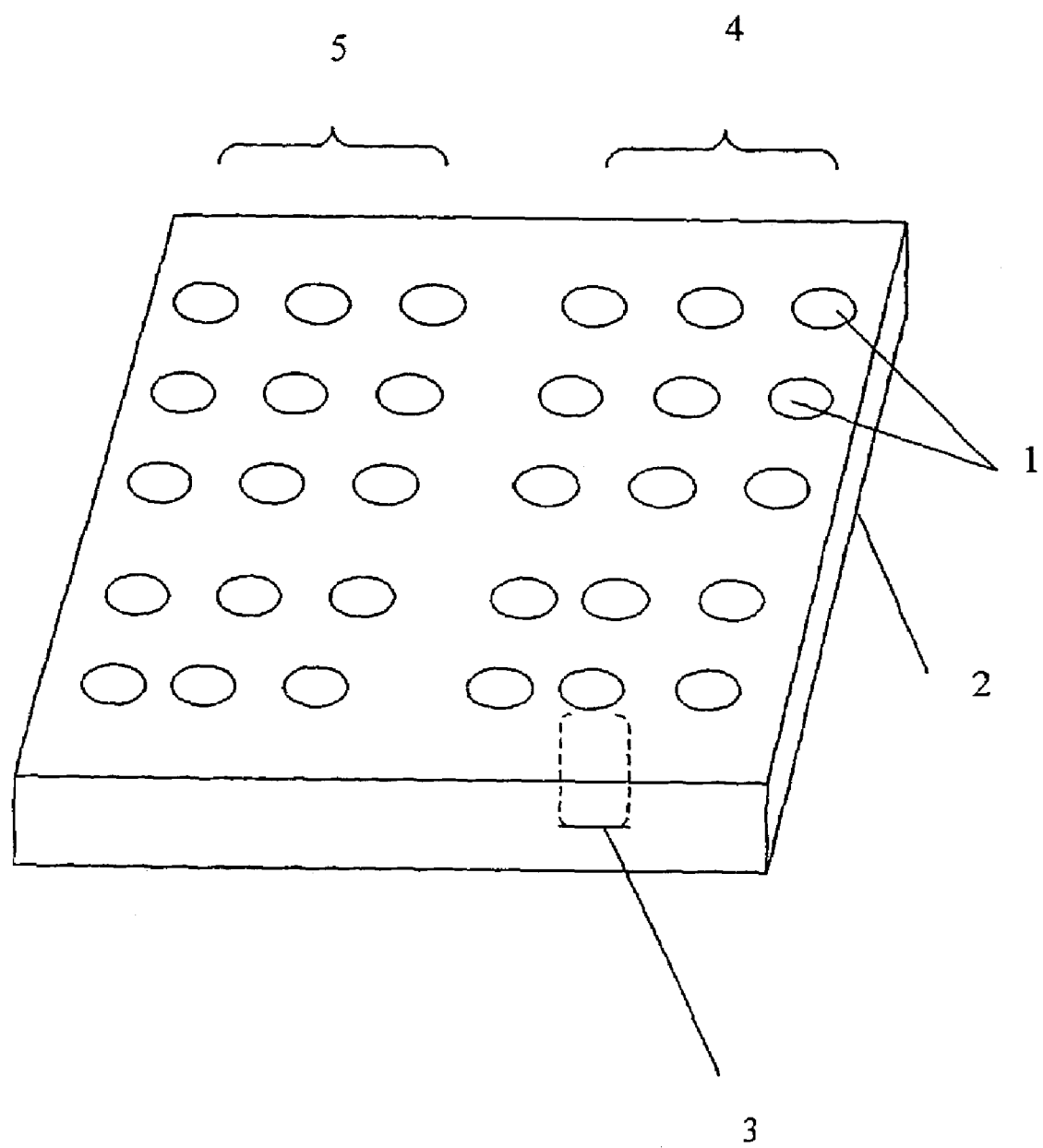
FIG. 1 is a schematic view of apparatus used in the method of the invention.

In the apparatus of FIG. 1, a plurality of wells (1) are provided in a plate (2) comprising an electrically conducting polymer which has been formed, for example by injection moulding, to contain the desired number of wells. Each well is provided with an electrode (3) which allows the content of the well to be heated using a predetermined thermal cycle by passing an electric current. The cycle within each well is controlled by electronic instrumentation (not shown).

The electronic instrumentation controls the time at which each amplification reaction is held at the extension phase temperature in the reaction.

Optionally also where the % GC content of the sample is to be analysed at the same time, using melt point analysis, different amplification reactions as a result of the use of different primer sequences, may be effected in some of the wells. Where this is done, it may be preferable to designate an area (4) of the plate (2) as a sample area and a separate area as a comparison area (5). A similar set of amplification reaction conditions and primers are effected in wells in the sample area (4) and the comparison area (5).

Sample nucleic acid is placed in each well in the sample area (4) whereas one or more nucleic acids of known origin or sequence are placed individually in wells in the comparison area (5). Amplification primers, nucleotides, buffers or other reagents necessary to carry out an amplification reaction are added to each well together with label means as described above and particularly an intercalating dye.

Current is then applied to each reaction vessel in a controlled manner such that it proceeds through thermal cycling to effect amplification with differing extension times. Luminescence from each well is monitored to detect the progress of the amplification reaction and to determine whether the extension time has been long enough to allow amplification to proceed.

In addition, optionally data concerned with the melting point of duplexes formed may also be gathered.

Figure 2:
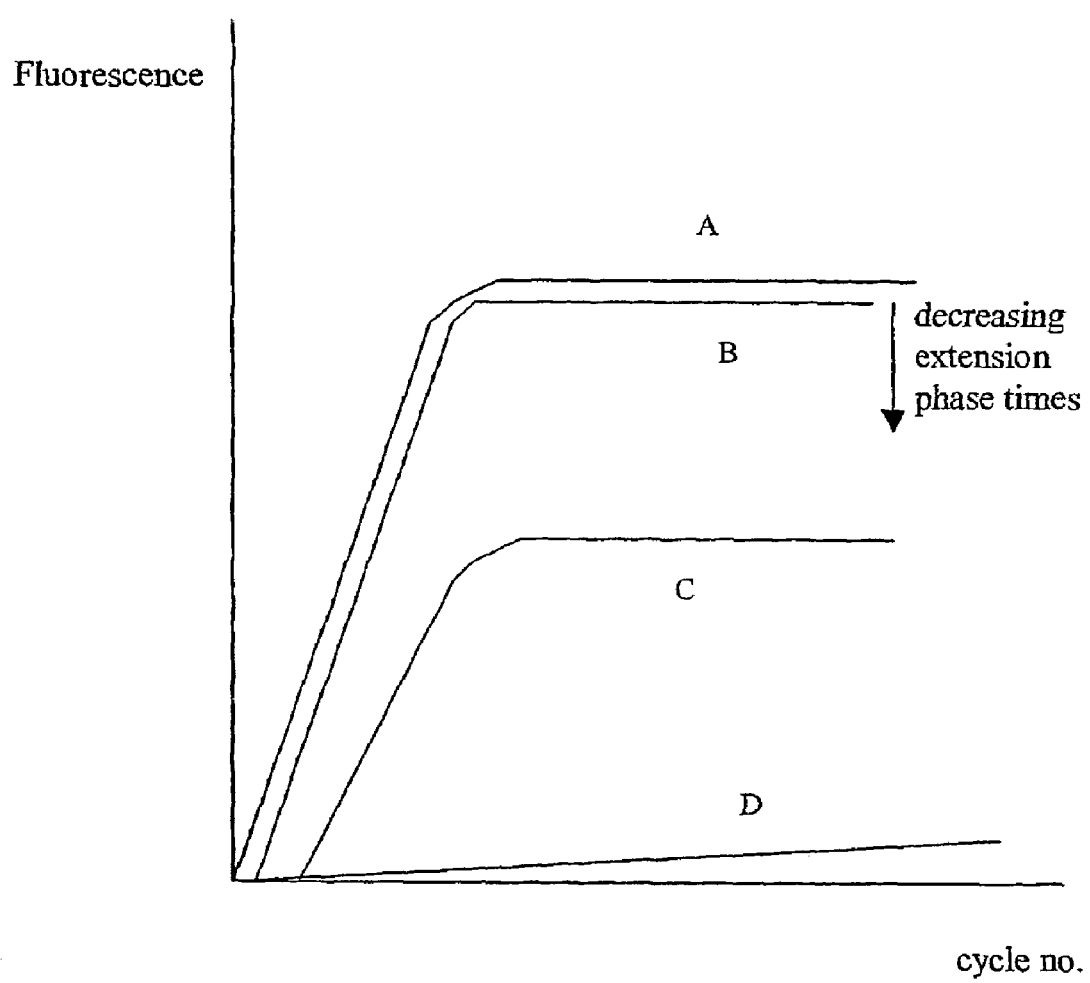
FIG. 2 illustrates the type of results which may be achieved using the method of the invention.

If the results are plotted on graphs of time versus luminescence as illustrated in FIG. 2, the sample amplification reactions will produce a series of sigmoidal curves, many of which (A, B), will be broadly similar in profile since the amplification reaction has proceeded normally and exponential amplification has occurred. However, where the extension time has not been long enough (D), only linear amplification from the original template will occur. In borderline cases (C), a marked diminution of the amplification reaction profile will be noted. This is because at this time, some product is successfully formed whereas others are just too short. This time can then be used to calculate sequence length.

Figure 3:
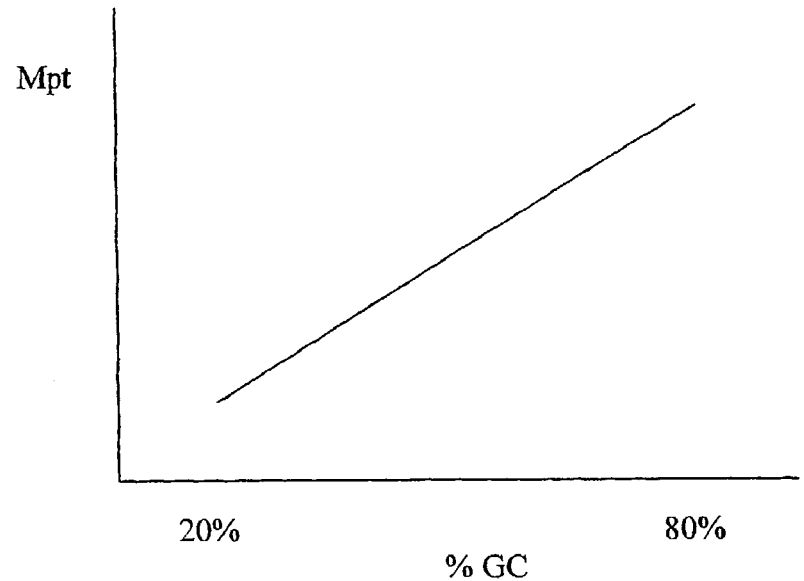
FIG. 3 illustrates the proportionality between the melting point and the % GC content for a given sequence length.

If at the same time melting points analysis is carried out, as different amplification reactions are used, a series of fluorescence vs melt temperature curves may be generated, corresponding to the melting points of the various sequences present within the sample nucleic acid. As discussed above, the melting point is a function of both the length of the sequence and the GC content. Thus, when combined with the results of FIG. 2, the absolute GC content of the sequence can be determined. This is because for a given sequence length, there is a directly proportional relationship between the % GC content and the melting point (FIG. 3).

Figure 4:
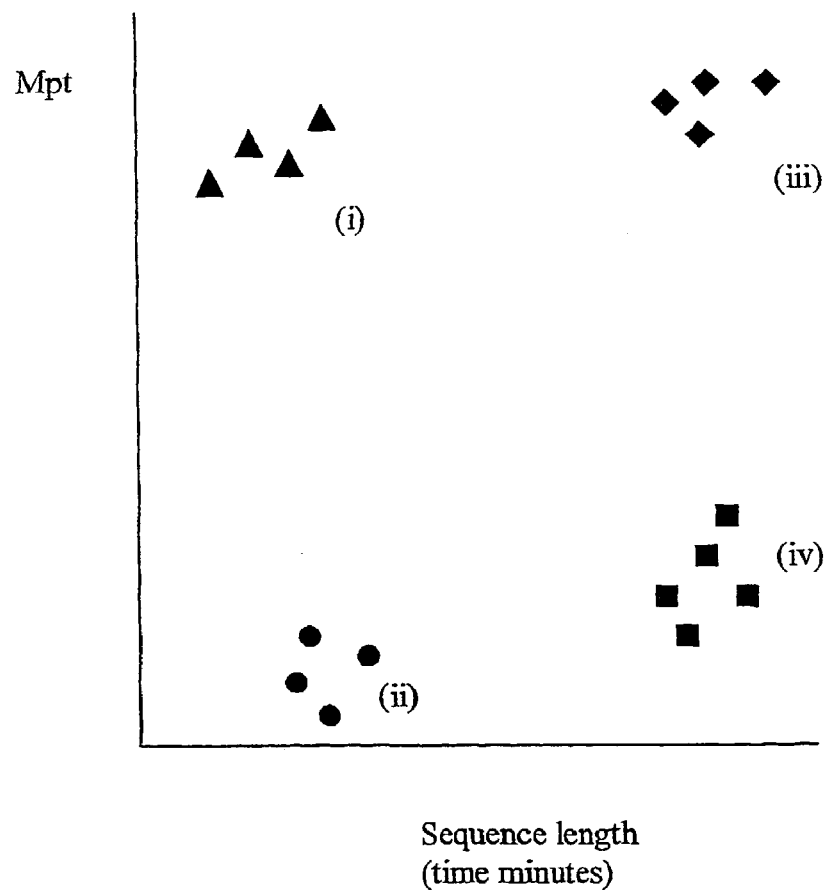
FIG. 4 shows plots of melting points vs length measurements for a range of products.

These results may be plotted to give a combined length (/melt profile of the sample nucleic acid from which the (taxonomically important) % GC content can be derived. An example of the sorts of comparative graphs which may be prepared is shown in FIG. 4. Since the sequence length is directly proportional to the minimum extension time, a similar graph would be obtained using the extension time results as the X axis.

It is clear here that the results in region (i) are produced by short products with relatively high % GC, whereas the results in region (ii) would be derived from short products with low % GC. Region (iii) results are derived from products of relatively long length with high % GC content and region (iv) results are derived from products of relatively long length with low % GC content.

Figure 5:
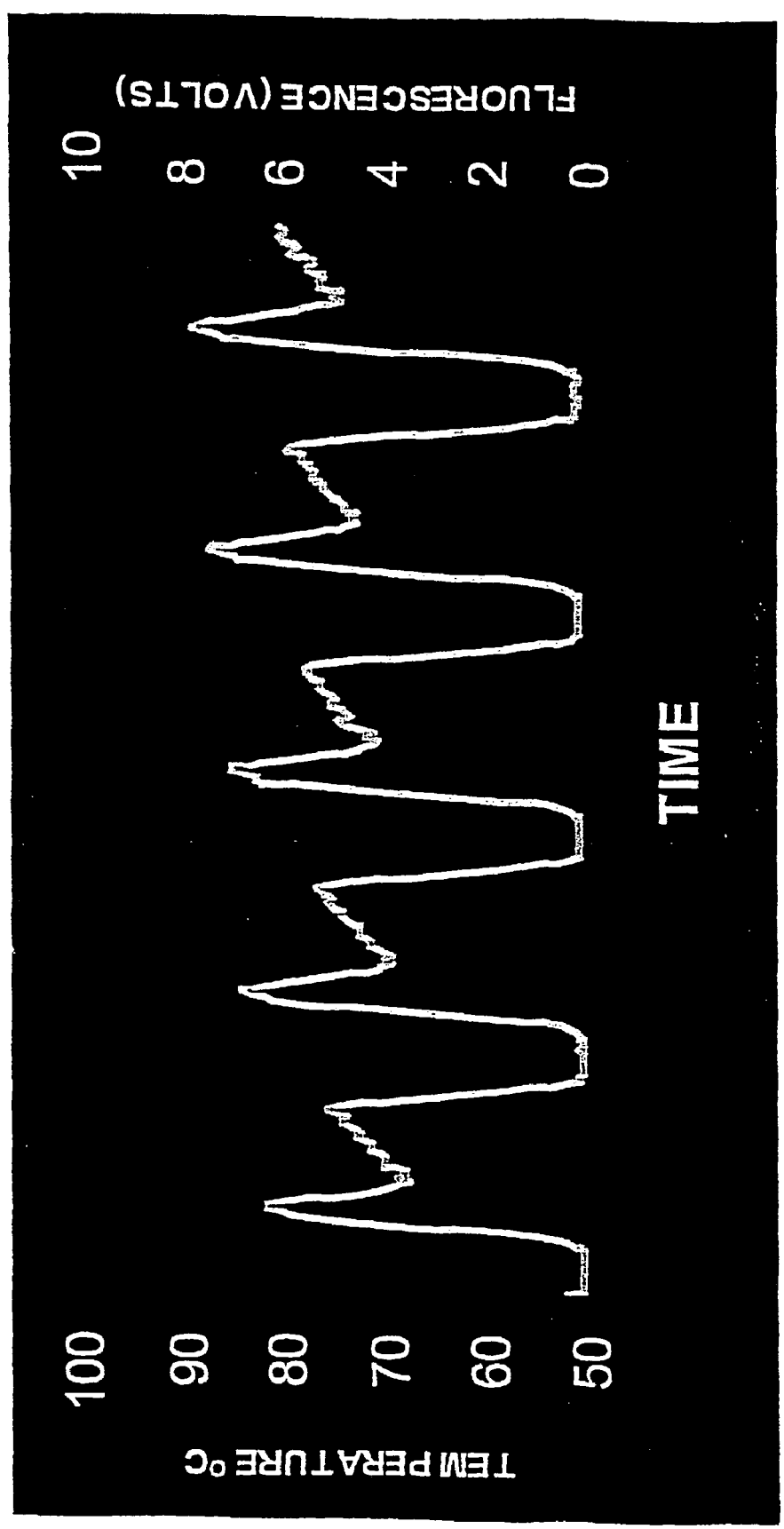
FIG. 5 shows the results of continuous monitoring of an amplification reaction when the reaction completely takes place.

When label means such as intercalating dyes are used as or as elements of the signaling system used to monitor the progress of the amplification, changes in the amount of duplex present in a reaction vessel can be monitored very clearly. As the amount of duplex increases, so the intensity of the fluorescent signal increases. If the fluorescence is monitored continuously though an amplification such as a PCR, a very characteristic pattern emerges as illustrated in FIG. 5. During the annealing phase of the reaction, a sharp peak of fluorescence occurs as a result of the large amount of duplex material in the reaction mixture. This drops significantly during the melt phase as the duplexes are destabilized and intercalating dye released, but gradually builds up again during the extension phase and double-stranded amplicon grows. The kinetics of the extension phase are relatively simple in an efficient amplification reaction and therefore, the monitoring curve at this time is broadly linear.

However, in the case of an incomplete reaction, in which the extension phase is too short to prepare full-length amplicon, the incomplete product may begin to act as a primer in subsequent cycles. The efficiency of such a reaction is lower than a reaction which uses the primer.

Consequently, the region (iii) of the fluorescence curve will change in shape and/or gradient as the reaction progresses.

This signal will work as an alternative or confirmatory way of detecting which reactions are not going to completion, and therefore will also lead to a determination of the less than optimum reaction times.

The invention claimed is:

1. A method of determining the length of a particular region of unknown length within a nucleic acid, said method comprising
    a) subjecting a sample of said nucleic acid to a plurality of amplification reactions in which said region is amplified by a polymerase having processivity, wherein the time of the extension phase in each of said reactions is varied;
    b) monitoring the progress of said amplification reactions;
    c) determining the minimum time required for the extension phase of the amplification to completely take place within each reaction mixture; and
    d) correlating the minimum time with a quantified processivity of the polymerase, thereby determining the length of the nucleic acid region.

2. The method of claim 1 wherein the amplification reactions comprise polymerase chain reactions.

3. The method of claim 1 wherein the said plurality of amplification reactions are effected simultaneously.

4. The method of claim 1 wherein each amplification reaction is effected in a well of a multiwell vessel, and each well is heated by supplying current to an electrically conducting polymer which comprises or is able to heat said well.

5. The method of claim 1 wherein the time of the extension phase of the amplification reaction in each well is independently controllable.

6. The method of claim 1 wherein the progress of the amplification reaction is monitored using a detectable label present in the reaction.

7. The method of claim 6 wherein said label comprises an intercalating dye.

8. The method of claim 6 wherein said label comprises a labeled probe.

9. The method of claim 8 wherein said labelled probe is a hybridization probe.

10. The method of claim 8 wherein said probe is a hydrolysis probe.

11. The method of claim 1 wherein in step (b), the progress of the extension phase is monitored continuously.

12. The method of claim 1 wherein the length of the particular region is used to screen clones obtained by recombinant DNA technology for the presence of concatamers.

13. The method of claim 1 wherein the length of the particular region is used in the diagnosis of genetic defects or viral infection or in DNA fingerprinting.

14. The method of claim 1 wherein the length of the particular region is used in linkage analysis.

15. The method of claim 1 wherein the length of the particular region is used in measuring the length of telomeres for age analysis.

16. The method of claim 1 wherein the temperature at which particular reaction products form duplexes or duplex forms destabilize within said sample is noted, and this information, combined with the determination of the length of the sequence, is used to calculate the percentage GC content of the sequence.

17. The method of claim 4, wherein the current to the electrically conducting polymer is effected by a control means set to control the current applied to the polymer to heat each well or group of wells individually.

18. The method of claim 17 wherein the control means is set to vary the time at which different wells are held at the temperature at which extension occurs during the amplification reaction.

19. The method of claim 17, wherein the control means is set to vary the temperature of the stage of the amplification reaction taking place in each well or group of wells.

* * * * *